United States Patent
Silva et al.

(10) Patent No.: US 9,323,075 B2
(45) Date of Patent: Apr. 26, 2016

(54) SYSTEM FOR THE MEASUREMENT OF THE INTERPUPILLARY DISTANCE USING A DEVICE EQUIPPED WITH A SCREEN AND A CAMERA

(71) Applicant: REVERSE ENGINEERING, LDA, Lisbon (PT)

(72) Inventors: Cesar Augusto dos Santos Silva, Lisbon (PT); Andre Filipe Marques da Silva, Almada (PT)

( * ) Notice: Subject to any disclaimer, the term of this patent is extended or adjusted under 35 U.S.C. 154(b) by 0 days.

(21) Appl. No.: 14/122,169

(22) PCT Filed: Feb. 8, 2013

(86) PCT No.: PCT/IB2013/051037
§ 371 (c)(1),
(2) Date: May 19, 2014

(87) PCT Pub. No.: WO2014/006516
PCT Pub. Date: Jan. 9, 2014

(65) Prior Publication Data
US 2015/0219934 A1 Aug. 6, 2015

(30) Foreign Application Priority Data
Jul. 3, 2012 (PT) .................................. 106430

(51) Int. Cl.
*A61B 3/11* (2006.01)
*G02C 13/00* (2006.01)
*A61B 3/00* (2006.01)

(52) U.S. Cl.
CPC ............ *G02C 13/003* (2013.01); *A61B 3/0025* (2013.01); *A61B 3/111* (2013.01); *G02C 13/005* (2013.01)

(58) Field of Classification Search
CPC ............ A61B 3/14; A61B 3/112; A61B 3/10; A61B 3/1005; A61B 3/12; A61B 3/152; A61B 5/0051; A61B 3/11
USPC ............ 351/204, 206, 246, 205, 200; 348/78; 345/728
See application file for complete search history.

(56) References Cited

U.S. PATENT DOCUMENTS

| 3,495,897 A | 2/1970 | Deforges |
| 4,845,641 A | 7/1989 | Hagiwara et al. |

(Continued)

FOREIGN PATENT DOCUMENTS

| CN | 102278978 | 12/2011 |
| DE | 10007705 | 2/2000 |

(Continued)

OTHER PUBLICATIONS

Espacenet, English Machine Translation of JP2004220069, Aug. 5, 2004.

(Continued)

*Primary Examiner* — Hung Dang
(74) *Attorney, Agent, or Firm* — Holland & Hart LLP

(57) ABSTRACT

The present invention is in the technical fields of optics and ophthalmology. The present invention relates to a system for the measuring of the interpupillary distance, defined as the distance between the left pupil center and the right pupil center, not requiring the use of any artifact or additional objects on the person's face, and using a conventional electronic device comprising a processor, a camera (201) and a display with high reflectivity (200).

6 Claims, 3 Drawing Sheets

(56) References Cited

U.S. PATENT DOCUMENTS

| | | | |
|---|---|---|---|
| 6,095,650 | A | 8/2000 | Gao et al. |
| 6,261,248 | B1 | 7/2001 | Takaishi et al. |
| 6,535,223 | B1 | 3/2003 | Foley |
| 6,791,584 | B1 | 9/2004 | Xie |
| 6,847,383 | B2 | 1/2005 | Agnew |
| 7,219,995 | B2 | 5/2007 | Ollendorf |
| 7,322,697 | B2 | 1/2008 | Jojiki |
| 7,665,843 | B2 | 2/2010 | Xie |
| 7,740,355 | B2 | 6/2010 | Sessner et al. |
| 8,231,220 | B2 | 7/2012 | Baranton |
| 2003/0123026 | A1 | 7/2003 | Abibol et al. |
| 2004/0004633 | A1 | 1/2004 | Perry et al. |
| 2005/0265604 | A1 | 12/2005 | Yuasa |
| 2007/0118428 | A1 | 5/2007 | Akiyama et al. |
| 2008/0201641 | A1 | 8/2008 | Xie |
| 2010/0195045 | A1* | 8/2010 | Nauche ............... G02C 13/005 351/204 |
| 2010/0220285 | A1 | 9/2010 | Simmonds |
| 2011/0242481 | A1 | 10/2011 | Wada et al. |
| 2011/0267578 | A1 | 11/2011 | Wilson |
| 2011/0317031 | A1 | 12/2011 | Honda |
| 2012/0016763 | A1 | 1/2012 | Kirschner |
| 2012/0257162 | A1 | 10/2012 | Encaoua et al. |
| 2012/0274902 | A1 | 11/2012 | Baranton et al. |
| 2013/0076884 | A1 | 3/2013 | Choukroun |

FOREIGN PATENT DOCUMENTS

| | | |
|---|---|---|
| FR | 1506352 | 12/1967 |
| GB | 2449855 | 12/2008 |
| JP | 2002034918 | 2/2002 |
| JP | 2004220069 | 8/2004 |
| KR | 100984550 | 9/2010 |
| WO | 2009007731 | 1/2009 |
| WO | 2011042623 | 4/2011 |
| WO | 2011113936 | 9/2011 |
| WO | 2011074769 | 11/2011 |
| WO | 2012022380 | 2/2012 |

OTHER PUBLICATIONS

Google Patents, English Machine Translation of CN102278978, Dec. 14, 2011.

Google Patents, English Machine Translation of WO2012022380, Feb. 23, 2012.

Warren Robinett et al., A Computational Model for the Stereoscopic Optics of a Head-Mounted Display, SPIE vol. 1457 Stereoscopic displays and Applications II, pp. 140-160, 1991.

Elmar T. Schmeisser et al., Analysis of Cardlab Data for Interpupillary and Vertex Distance: Notes on the Construction of an "Eye-Box", United States Air Force Research Laboratory, pp. 1-17, Jul. 1998.

Carlos Hitoshi Morimoto, Automatic Measurement of Eye Features Using Image Processing, Departamento de Ciencia da Computacao, pp. 1-11, Dec. 31, 2009.

Andrew Winters, Bringing Eyewear Measurement Into The 21st Century, VCPN, http://www.totallyoptical.com/...7027421841978F18BE895F87F791&tier=4&id=E6466401ABEF46358A158E6049F93E07&AudID=28EBA89F5F874675BCE10DE3DCF0D05B, pp. 1-2, Oct. 2008.

Optician, Phone enables online buyers to measure PD, http://www.opticianonline.net/Articles/2010/08/27/26151/iPhone+enables+online+buyers+to+measure+PD+.html, pp. 1-2, Aug. 27, 2010.

Shay Rootman, YouTube Video, Mychic Augemented Reality Pupils Distance PD measure tool, http://www.youtube.com/watch?v=NEx3BiiXbZc, uploaded on Mar. 29, 2012.

TechWench, New iPhone App Solves Worries About PD When Buying Glasses Online, http://www.techwench.com/new-iphone-app-solves-worries-about-pd-when-buying-glasses-online, pp. 1-10, Nov. 21, 2011.

Vistech Projects, Android App: Partometer-Camera Measure, http://www.4androidapps.net/apps/partometer-camera-measure-download-198010.html, pp. 1-13, Mar. 13, 2012.

Rob Dewhurst, Android App: Pupil Meter, https://play.google.com/store/apps/details?id=air.PupilMeterAnd, pp. 1-2, Dec. 13, 2010.

Just Eyewear, Pupilmeter, http://www.justeyewearcom/pupilmeter, pp. 1-2, Feb. 9, 2011.

Rob Dewhurst, Ipad App: Pupilo Meter Pro, https://itunes.apple.com/us/app/pupil-meter-pro-for-ipad/id399778692, pp. 1-2, Dec. 5, 2011.

Espacenet, English Abstract of JP2002034918, Feb. 5, 2002.

Google Patents, English Abstract and English Machine Translation of DE10007705, Feb. 19, 2002.

Swennen et al., A new method of 3-D cephalometry Part I: the anatomic Cartesian 3-D reference system, The Journal of Craniofacial Surgery, pp. 314-325, Mar. 2006. (Only abstract provided).

* cited by examiner

SYSTEM FOR THE MEASUREMENT OF THE INTERPUPILLARY DISTANCE USING A DEVICE EQUIPPED WITH A SCREEN AND A CAMERA

TECHNICAL FIELD AND BACKGROUND ART

The present invention is in the technical fields of optics and ophthalmology. The present invention relates to a system for the measuring of the interpupillary distance through an optical process, without physical contact.

In the prescription of corrective eyeglasses it is necessary to have knowledge of several biometric data regarding the dimensions and shape of both face and the visual system of the patient, including the respective frame supporting the lenses. Knowing these data, it is possible to obtain personalized lenses which are able to correct the patient visual deficiency. Among these biometrical data, one of uttermost importance is the Interpupillary Distance, defined as the distance between the centers of the pupils.

The Interpupillary Distance is a crucial information on the creation of ophthalmic lenses, since it defines the distance from the optical axis of both lenses to place in the frame. A correct measurement of this distance is determinant for a perfectly corrected eyesight. An incorrect measure of this distance (more than 1 mm) will create a misalignment of the lenses relative to the eyes, which may lead to imperfect vision and eye strain.

Further biometrical data relevant for the lens design are: the distance from the center of the pupil to the patient's nose, known as mono-pupillary distance; the distance from the center of the pupil to the lens, traditionally known as the vertex distance and the inclination angle of the lens relative to the optical axis.

Several systems have been developed to measure the Interpupillary Distance, however most of them are complex and costly, and are mainly used by specialized technicians, mostly optometrists and ophthalmologists in specific places, such as clinicals or opticians. These systems are, in general, quite accurate and can take measures with an error of less than 1 mm, they use specialized machinery and typically require extra objects to be placed above the patient's face or over the frame. The most relevant systems and the ones most related to this invention are the following:

a) Optical only systems: One of the most used classical system is the Pupilometer, described in the patent FR1506352. This device, composed of a set of lenses, contains three openings, two of them reproduce the glasses lens structure and shall be placed in contact with the patient nose. The remaining one is placed in the opposite side, from where the Measurer will look, with his eye placed in the focus point of a collimator lens. This lens allows for the light source, contained in the device, to be placed in the infinity, which simulates distance vision. The lens can also be movable, which enables the measurement of the Near Interpupillary Distance. The Measurer can move two markers such that both are aligned with the patient pupils, determining the Interpupillary Distance in that way. These systems are specially constructed for this lengthy process, which requires the active participation of a technician.

The presented invention uses a different technological principle, since it eliminates the participation of the technician and allows the patient to measure his own Interpupillary Distance using a device that is accessible most of the time, such as a tablet, smartphone or a laptop computer.

b) Optical systems with artifacts over the face or frame: Recently, a new set of commercial systems were presented, which are based in a image sequence, such as the system described in patent WO 2011/042623. Their principles are based on the capture of a sequence of images of the patient's face from different perspectives. It is necessary to place an object with predefined markers above the patient's face or frame. This artifact is crucial to obtain a geometric relationship between the pictures. The present invention, unlike the latter, neither needs any device on the patient's face, nor requires the patient to carry out a set of poses.

c) Optical systems with user movement: The system WO 2011/113936 is also based in a set of photographs, in which the patient makes a predetermined set of movements and, unlike the previous ones, requires no artifact on the face or frame for measuring the Interpupillary Distance. This system applies a statistical calculation which is based on an iterative optimization algorithm for estimating: the distance to the camera, the Interpupillary Distance, the focal length of the camera, the radius of the eyeball and the pupil size, taking into account all images from a sequence of photographs taken from the patient movements. No results are known regarding the exactness on the estimation of this multi variable problem. In addition to the necessary computational burden, this system requires the patient to conduct a predetermined motion, and depends on the automatic detection of the circle around the pupil, which can be difficult since it requires sophisticated methods of detection and a high camera resolution.

The present invention, unlike the previously described system, requires no patient movement, since the measurement is obtained from a single photography. Additionally, the Distance estimation is based on simple calculations of elementary geometry, requiring no computational burden at all.

d) There are other systems that can locate the pupil three-dimensionally, using stereo vision systems (with multiple cameras or a moving camera) or using active processes for detecting the distance from the patient to the system, such as the patented system WO2009/007731, or the case of systems with structured light scanning, such as CN101739717. These systems can be quite accurate in metric terms, however they use specific hardware devices which are highly calibrated and costly. In some cases they are obtrusive or bothersome to the patient, as is the case of the systems which use structured light systems.

The present invention uses a different technological principle than these systems: it is non-intrusive and easy to implement in a conventional device, which is available to most people, such as a laptop, tablet or smartphone.

In recent years, the market for online sale of lenses and frames has increased significantly and the offer is diverse. This context arises with a new need: obtaining the Interpupillary Distance of the patient remotely, discarding the inconvenience of paying a visit to a specialized technician. If someone opts to acquire his new glasses in an online retail shop, it is necessary to know what his Interpupillary Distance is previously, and the only reliable way to obtain it is to perform the measurements in an ocular specialist. This inconvenience eliminates the main advantage of online sale: buying without the physical presence of the customer. Thus, to obtain the Interpupillary Distance, some online retailers are asking their customers to apply rudimentary techniques of measurement, based on objects placed in front the patient's face or forehead or based on direct measurement with a ruler. These techniques are based on empirical or approximate geometric principles and therefore produce erroneous results, whose measuring errors may exceed 3 mm. These procedures are generally discouraged by optometrists.

The first of these systems corresponds to a simple direct measurement with a ruler, which involves multiple measurement errors due to the distance from the ruler to the measured object. The errors are significant and difficult to quantify. When the measurement is performed in front of a mirror, the error will be even higher.

There are a few more rigorous systems which use only one camera and an extra object with known marks or dimensions that must be placed over the patient's face. Examples of these systems include objects such as credit cards or target aims to be placed over the patient forehead or above the patient's frame (system proposed in US patent 2011/0267578). These systems assume that the artifact is co-planar with the centers of the pupils, which never happens. Moreover, the method is very dependent on good use of the artifact by the user. Thus, to the measurement error contribute not only parallax errors, but also errors due to frequent misuse of the artifact.

Unlike previous systems, the present invention does not need extra artifacts or rulers on the face of the patient and the results obtained are not an approximation of reality.

DISCLOSURE

General Description

The system described herein allows a user to measure the Interpupillary Distance using a conventional device with the following requirements: having processing capacity, being provided with at least one camera and having a screen with a reflective capacity. We can find examples of such devices on laptops, tablets, smartphones, PDAs and mobile phones.

The present invention, following the configuration present in FIG. 3, uses the reflective property of the device screen surface (300), which working as a mirror, allows the user to see his own reflection (302). The user aligns the centers of both pupils above a marker drawn on the screen (303), generating a geometrical restriction that places both eyes in a plane (308). The device camera (301) detects the centers of the pupils, estimating the projection ray of the left pupil (309) and the projection ray of the right pupil (310). The location of the pupil centers and the distance between pupils is obtained by the intersection of the said projection rays (309) and (310) with the plane (308).

DETAILED DESCRIPTION OF THE INVENTION

The present invention has the following advantages or differences when compared to existing systems:
  a) The system eliminates the use of specialized equipment for this purpose or a third person, as in the referred inventions: FR1506352, WO2011/042623, WO 2009/007731;
  b) The system eliminates the need for rulers or any artifact on the face or on the frame, as in inventions WO2011/042623 or U.S. 2011/0267578;
  c) The system calculates the Interpupillary Distance based on just a photograph, eliminating the need for multiple shots forcing a particular movement of the user, such as the invention WO 2011/113936;
  d) The system is non-intrusive and easy to implement on a large consumption device, available to most people, such as laptops, tablets or smartphones.
  e) The system is accurate, with an error of less than 1 mm, unlike many systems using empirical methods and approximated results, as U.S. 2011/0267578.

DETAILED DESCRIPTION OF THE INVENTION

The present invention is hereafter described with further detail, without limitation and by way of example, showing forms of preferred usage, depicted in the annexed pictures, wherein FIGS. 2 to 5 are a schematic and simplified representation of the system, according to the invention.

Figure 1:
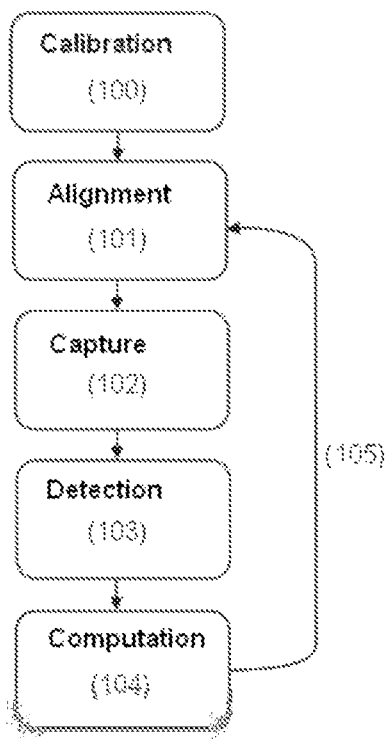
FIG. 1 represents the general execution steps of the method.
Figure 2:
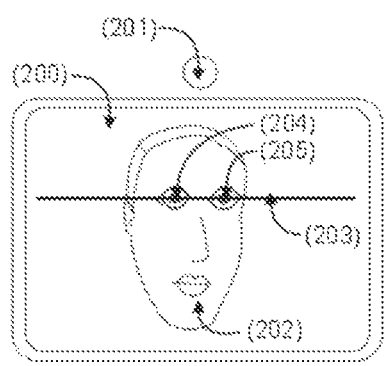
FIG. 2 represents the reflection of the User face in the device screen.
Figure 3:
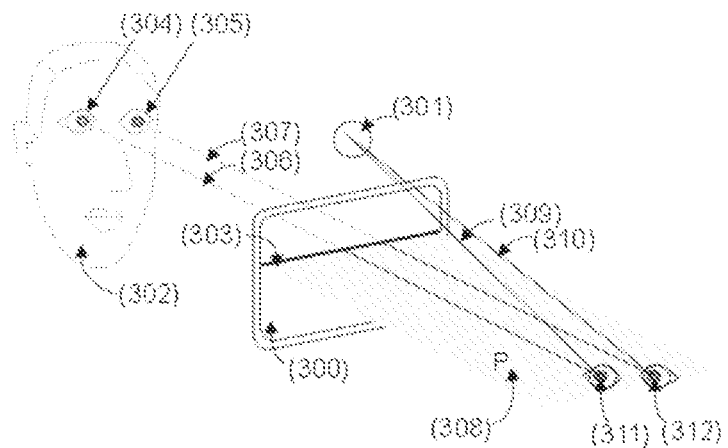
FIG. 3 depicts a schematic representation from a perspective viewpoint.
Figure 4:
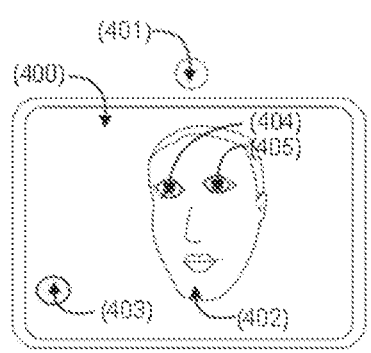
FIG. 4 represents the User picture captured by the camera and shown in the d device screen.
Figure 5:
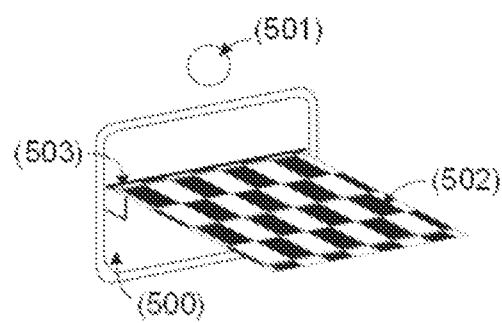
FIG. 5 shows a representation for the system calibration.

The present invention corresponds to a measurement system, subject of claim 1, comprising:
  1. A device controlled by a processor, incorporating a screen with high degree of reflectivity (200) (300) (400) and a camera (201) (301) (401) with a marker on the screen (203) (303).
  2. A system to obtain measures based on reflection (202) (302) of the object to be measured using the device display as a reflective mirror (200) (300).
  3. A system to obtain the Interpupillary Distance based on the combination of the reflection of the pupils of the user and the points from the image captured by the camera which are respectively the points (204) and (205), and points (404) and (405).

Most displays of conventional devices are reflective enough to function as a mirror, such that it is possible to see the User's reflection (202) on it, specially when the background of said display is black and under adequate light conditions. Moreover, the device camera can capture a picture of the face of the User (402) under the camera point of view. Both the reflection and the camera picture, create together two different viewpoints of the same object at the same time, creating therefore a stereo pair, which in computer vision, allows the obtention of three dimensional information with great accuracy, regarding that the geometrical relation between the two different "views" are known a priori. Thus, by knowing the location of points (204) and (205) corresponding to the same centers detected in the picture, it is possible to determine the three dimensional location of the pupil centers by a computational method, which is explained below through a set of steps, depicted in FIG. 1 and the subject of claim 2:

(100) The first step is a calibration routine common to all measuring systems, whose purpose is to find the geometric relationship between the elements of the device.

(101) The second step consists on the alignment of the User in front of the device screen. The present invention uses the reflective properties of the surface of the device screen which working as a mirror lets the user see the reflection of his own face (202) (302). The User must, therefore, align his pupils' reflection with the visible marker (203) (303) drawn on the screen. The marker can be a pair of points (to align with the center of the pupils), or two circumferences (to be filled with the pupils reflection), or a line segment (intersecting the center of the pupils) or any other equivalent geometric shape that is able to restrict the pupil centers over a pre-established straight line. This alignment process automatically ensures that the centers of the pupils are over a known plane (308).

(102) When the User considers himself perfectly aligned, it is time to move on to the third step consisting on capturing a picture (402) of his face from the camera (401).

(103) The fourth step consist on the detection of the location of the center of the two pupils (404) and (405), in the previously obtained picture. This can be achieved by a manual process wherein the user clicks on the points of interest or through an automatic eye-detection process in the image.

(104) The fifth step involves determining the three-dimensional position of the center of the left pupil (304) and the center of the right pupil (305). Restricting the centers of the pupils to two points in the image—in step (103)—is equal to restrict the location of the centers of the two projection rays (309) and (310). Thus, the three-dimensional locations of the centers of the pupils can be found through the intersection of the said rays on the projection plane (308) found in step (101).

In this last step, it is determined the most important optometric distance over the plane (308), with implications in the definition of ophthalmic lenses, that is the distance between the center of the pupils, the Interpupillary Distance.

It is possible to repeat the process for the same or another user, by returning to step (101).

The generalization of the method, the subject of Claim No. 3, can be made to the three dimensional position of any arbitrary points defined on the plane (308), either belonging to the user's face or belonging to a frame or lens placed over the face, including some points of great optometric importance, such as:
  a) the point on the axis of symmetry of the nasal dorsum, used to calculate the left and right nasal-pupillary distance, defined as the distance from the sagittal plane passing through this point to the center of the left and right pupil, respectively;
  b) the two inner extreme points of the right and left lenses, used to calculate the size of the bridge, defined as the distance between the inner ends of the two lenses;
  c) external points in the lenses and frame;
  d) the point on the lens that is intersected by the optical axis of the User, used to calculate the vertex distance, defined as the distance between that point on the lens and the center of the pupil.

To obtain the three-dimensional position of these points, they have to be detected manually or automatically on the picture (402) with their position calculated from the intersection of the projection ray of the point on the image with the plane P (308).

Variants

The first variant, the subject of Claim No. 4, consists in estimating the three-dimensional position of generic points which are approximately at the same distance from the user pupils to the screen. This approximation might be useful to estimate the distances of points, which while being placed outside the plane P (308), its distance to the camera is similar to the distance to the pupils, such as points on the eyes, the eyebrows or points on the frame. This model, known as paraperspective model assumes that the third coordinate (depth) is constant and equal to the third coordinate of the center of the pupils, whereby the two other coordinates are obtained using the coordinates of the camera.

The second variant, the subject of Claim No. 5 is the ability of the method to be used in a set of images or a sequence of photographs obtained for different poses of the user, in order to calculate specific features of the Interpupillary Distance of the User for different situations. More specifically, the method can be applied to obtain various instances of the Interpupillary Distances, especially for near vision, medium distance vision or vision directed to infinity. To obtain the various distances, it is possible to vary the screen relative to the user, asking him to keep his eyes to converge on his own reflection. The viewing distance, for each picture, is given by the distance between the User and his reflection (equivalent to twice the distance from the user to the screen).

Assumptions

The present invention takes the following assumptions:
  a) the camera (201) (301) (401) is calibrated, that is, its intrinsic parameters are known a priori, such as focal length, distortion parameters and the optical center.
  b) the screen (200) (300) (400) is reflective, allowing the visualization of the reflection of the User in the glass screen, if this is dark and if the face is well lit. The likely effect of double reflection due to multiple layers of glass present on the screen is considered negligible.
  c) the screen (200) (300) (400) is entirely flat.
  d) the camera (201) (301) (401) is calibrated relatively to the display (200) (300) (400), i.e. the extrinsic parameters that relate the camera and the plane are known beforehand.

If the assumptions a) and d) are not verified, that is, if the calibration parameters are not known a priori, they can be obtained by a calibration step (100), using, for that purpose, a planar calibration object (502). This object is constructed out of a rigid material with matte-finish, whose dimensions are approximately the same of said screen. In this object a regular checkerboard pattern is drawn or printed, whose dimensions are known with great accuracy The geometric relationship between the screen and the camera can be estimated using the following steps:
  a) place the said flat calibration object (502) above the screen (500), keeping it perpendicular to the plane of the screen;
  b) adjust said calibration object to the lien defined by said marker (503) visible on the screen, such that the object plane intersects the plane of the screen exactly in the line of said marker; thus the object plane (502) is coincident with plane (308);
  c) ensure that the camera (501) displays the total or partial checkerboard pattern of the object. If the camera does not display the grid, it should be repositioned, if possible, otherwise a new calibration object with larger dimensions must be produced;
  d) obtain a photograph and detect the corners of the gird displayed in the image, through a manual or automatic method;
  e) calculate the geometric position of plane (308) relative to the camera, based on the known dimensions of the checkerboard pattern of the said calibration object.

INDUSTRIAL APPLICABILITY

The use of the system, subject of claim 6, can be found in any of the following applications:
  a) Estimation of ophthalmic measures aiming at the planning and construction of monofocal and progressive ophthalmic lens, for its sale either in physical retail stores or online retail;

b) A survey of three-dimensional scaffold for building custom-made frames either in physical stores or in online retail;

c) Obtention of ophthalmic measures for choosing lenses and frames from a database or for aesthetic or medical advice of lenses or frames that fit the user best;

d) Collection of ophthalmic data for multimedia applications in physical or online stores for the visualization of virtual lenses and frames over the client's face in the form of augmented reality;

e) The system is not limited to application of optometry and may also be extended for aesthetic, cosmetic and reconstructive medicine applications, such as aesthetic eyebrows, lips, hair, makeup, tattoos and for pre and post cirurgical cosmetic and reconstructive medicine.

The invention claimed is:

1. A system for the calculation of the Interpupillary Distance, defined as the distance between the center of the left pupil (304) and the center of the right pupil (305) of a User, comprising:
   a) a processor that controls all other resources, performs automatic processing of data acquired by said camera and manages the results and user interface;
   b) a planar screen (200)(300)(400)(500) where images can be visualized;
   c) a camera (201)(301)(401)(501) which acquires images;
   d) a structure that rigidly attaches said camera and said screen;
   e) a planar calibration object (502) with a printed calibration pattern used to calibrate or estimate the geometric relation between said camera and said screen;
   f) a marker (203)(303), drawn in or placed above said screen, whose function is to allow the alignment of the User pupils with the shape of a line segment of white color or any other contrasting color with the black background of said screen, superimposed over said screen or drawn by the system to appear on said screen, wherein the shape of said marker can be a line segment, two points to align with the pupil centers, two circumferences, or any other shape that allows the alignment of the pupils in a straight line;
   g) a cover surface of said screen (200)(300)(400)(500) with reflective property, which working as a mirror, allows said User to see the reflection of his face (202) (203) and simultaneously, when the pupils are aligned with said marker, restricts geometrically the location of the pupils and their reflection to a unique plane P (308) perpendicular to said screen containing the said marker.

2. Method to calculate the Interpupillary Distance using the system according to claim 1, comprising:
   a) a calibration step (100) for the calculation of the geometric relationship between said screen (200) and said camera (201) and the estimation of said plane P (308);
   b) an alignment step (101) performed by said User, aided by his own reflection (302), consisting in aligning the pupils with said marker (203) (303);
   c) a step of capturing a photograph (102) of said User's face with said camera (401), when the user considers himself aligned with said marker (203)(303);
   d) a detection step (103) of the centers of the pupils in said image, photographed in the previous step, performed by a manual selection of the centers of the pupils, which is equivalent to estimate the projection rays (309) and (310) of the two pupils;
   e) a step of calculating the Interpupillary Distance (104) that calculates the distance between said pupils (404) (405) on the picture (402) from the distance between the three-dimensional positions of the centers of the pupils given by the intersection of said projection rays (309) and (310) of the pupil centers, found in the previous step, with said plane P (308) estimated in the first step.

3. Method for calculating the Interpupillary Distance according to the claim 2, wherein it allows the generalization of the calculation of the three dimensional position of any point of said generic plane P (308), which belongs either to the user's face, either to the frames or to the lens placed over the User's face, provided that said point is selected on said photograph (402) captured by said camera (201), and the calculation of the three dimensional position of said point is given by the intersection of the respective projection ray with said plane P (308).

4. Method of calculation according to claim 2 wherein it can be extended to calculate the three dimensional position of any point at the same depth of a reference point belonging to said plane P (308), provided that said depth is given by the distance of said reference point to the plane of said screen and said three-dimensional position of said point is given by the intersection of the projection ray of said point on the plane parallel to said screen containing said reference point.

5. Method for calculating the Interpupillary Distance, according to claim 2, wherein it applies for various vision distances, from near vision to far vision, such that to obtain the Interpupillary Distance for each said vision distance, it is necessary to change the distance from said screen to said User, providing that the User eyes converge to his own reflection in said screen and said vision distance is the distance from the User to his reflection.

6. Usage of the system and measuring method and estimation of optometric measures according to claim 2, wherein it can be applied to any of the following applications:
   a) the planning, cut and construction of ophthalmic monofocal or multifocal lenses;
   b) construction of custom-made frames;
   c) selection of lenses and frames that best fit the User;
   d) multimedia applications for the visualization of virtual lenses and frames over the User's face in the form of augmented reality.

* * * * *